(12) United States Patent
Nishino et al.

(10) Patent No.: US 7,858,807 B2
(45) Date of Patent: Dec. 28, 2010

(54) METHOD FOR PRODUCING 1-SUBSTITUTED-5-ACYLIMIDAZOLE COMPOUND

(75) Inventors: Shigeyoshi Nishino, Yamaguchi (JP); Shuji Yokoyama, Yamaguchi (JP); Hiroyuki Oda, Yamaguchi (JP); Yoji Omata, Yamaguchi (JP); Shinya Takigawa, Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 12/064,433

(22) PCT Filed: Aug. 22, 2006

(86) PCT No.: PCT/JP2006/316431

§ 371 (c)(1),
(2), (4) Date: Feb. 20, 2009

(87) PCT Pub. No.: WO2007/023822

PCT Pub. Date: Mar. 1, 2007

(65) Prior Publication Data

US 2009/0306399 A1 Dec. 10, 2009

(30) Foreign Application Priority Data

Aug. 23, 2005 (JP) .............. 2005-241494

(51) Int. Cl.
*C07D 233/64* (2006.01)
*A61K 31/4172* (2006.01)
(52) U.S. Cl. .................. 548/333.5; 514/399
(58) Field of Classification Search .............. 548/333.5; 514/399
See application file for complete search history.

(56) References Cited

U.S. PATENT DOCUMENTS

| 4,482,723 A | 11/1984 | Reiter |
| 2005/0131000 A1 | 6/2005 | Newcombe et al. |

FOREIGN PATENT DOCUMENTS

| AU | 5082779 | 3/1980 |
| AU | 2669384 | 10/1984 |
| DE | 2839989 | 4/1980 |
| EP | 0009163 | 4/1980 |
| EP | 125777 | 11/1984 |
| EP | 0125777 | * 11/1984 |
| JP | 55-040689 | 3/1980 |
| JP | 59-205365 | 11/1984 |
| JP | 2004-256550 | 9/2004 |
| WO | WO 94/06776 | 3/1994 |
| WO | WO 03/076436 | 9/2003 |

OTHER PUBLICATIONS

Shilcrat et al. "A New Regioselective Synthesis of 1,2,5-Trisubstituted 1H-Imidazoles and Its Application to the Development of Eprosartan" Journal of Organic Chemistry 62(24):8449-8454 (1997).
Reiter et al. "Synthesis of 4(5)-acyl-, 1-substituted 5-acyl- and 1-substituted 4-acyl-1H-imidazoles from 4-aminoisoxazoles" Journal of Organic Chemistry 52:2714-2726 (1987).
Supplementary European Search Report issued in the corresponding European Patent Application No. 06796645.7 (Mar. 29, 2010).

* cited by examiner

*Primary Examiner*—Joseph K. McKane
*Assistant Examiner*—Janet L Coppins
(74) *Attorney, Agent, or Firm*—Morgan Lewis & Bockius LLP

(57) ABSTRACT

Disclosed is a commercially suitable method for producing a 1-substituted-5-acylimidazole compound. A 1-substituted-5-acylimidazole compound is produced with a high position selectivity by reacting an N-substituted amidine compound or a salt thereof with a ketone compound in the presence of a base.

23 Claims, No Drawings

METHOD FOR PRODUCING 1-SUBSTITUTED-5-ACYLIMIDAZOLE COMPOUND

RELATED APPLICATIONS

The present application is a U.S. National Phase Application of International Application No. PCT/JP2006/316431 (filed Aug. 22, 2006) which claims the benefit of Japanese Patent Application No. 2005-241494 (filed Aug. 23, 2005), both of which are hereby incorporated by reference in their entirety.

FIELD OF THE INVENTION

The present invention relates to a process for preparing 1-substituted 5-acylimidazole compounds. The 1-substituted 5-acylimidazole compounds are useful as starting compounds and intermediate compounds for preparing pharmaceutically active compounds or agricultural chemicals. Particularly, the 1-substituted 5-acylimidazole compounds can be used for preparing pyrimidine compounds which have cell cycle inhibitory action (for example, pyrimidine compounds described in PCT applications such as WO 02/20512, WO 03/076433, WO 03/076434, WO 03/076435 and WO 03/076436).

BACKGROUND OF THE INVENTION

Heretofore, there have been known two processes for preparing 1-substituted 5-acylimidazole compounds.

J. Org. Chem., 52, 2714 (1987) describes a process for preparing 5-acetyl-1-benzyl-2-methylimidazole which comprises steps of reacting 5-methylisooxazole and ammonium nitrate in trifluoroacetic acid anhydride to give 5-methyl-4-nitroisooxazole, reducing the 5-methyl-4-nitroisooxazole with aluminum amalgam to give 5-methyl-4-aminoisoxazole, subjecting the 5-methyl-4-aminoisoxazole to benzylation and acetylation to give N-benzyl-N-(5-methyl-4-isoxazole)acetamide, and reducing the N-benzyl-N-(5-methyl-4-isoxazole)acetamide. This process is industrially disadvantageous in that the process requires a large number of steps and its overall yield is such low as 28%.

J. Org. Chem., 62, 8449 (1997) describes a process for preparing a 5-formylimidazole compound which comprises reacting an amidine compound and 2-bromo-3-(1-methylethoxy)-2-propenal in chloroform in the presence of potassium carbonate (yield 33-83%). This process is industrially disadvantageous because the reaction yields are variable and low, and a small amount of a structural isomer (i.e., 4-formylimidazole) is observed in addition to the desired 5-formylimidazole.

SUMMARY OF THE INVENTION

The present invention has an object to provide an industrially advantageous simple process for preparing a 1-substituted 5-acylimidazole compound in a high yield.

The invention resides in a process for preparing a 1-substituted 5-acylimidazole compound having the following formula (1):

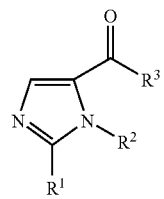

in which $R^1$ is a hydrogen atom or a hydrocarbyl group which has or does not have a substituent group, $R^2$ is a secondary alkyl group, a tertiary alkyl group or a cycloalkyl group, said group having a substituent group or no substituent group, and $R^3$ is a hydrocarbyl group which has or does not have a substituent group, which comprises reacting an N-substituted amidine compound having the following formula (2):

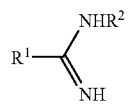

in which each of $R^1$ and $R^2$ has the above-mentioned meaning, or a salt thereof with at least one ketone compound having the following formula (3a) or (3b):

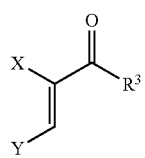

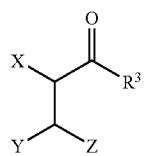

in which $R^3$ has the above-mentioned meaning, X is a leaving group, and each of Y and Z independently is a halogen atom, an alkoxy group, an aryloxy group, an alkylthio group, an arylthio group, a dialkylamino group or a diarylamino group, in the presence of a base.

The invention further resides in a process for preparing a 1-substituted 5-acylimidazole compound having the following formula (1):

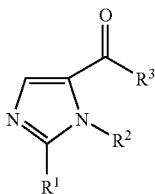

(1)

in which $R^1$ is a hydrogen atom or a hydrocarbyl group which has or does not have a substituent group, $R^2$ is a secondary alkyl group, a tertiary alkyl group or a cycloalkyl group, said group having a substituent group or no substituent group, and $R^3$ is a hydrocarbyl group which has or does not have a substituent group, which comprises a step of reacting an imido-acid compound having the following formula (4):

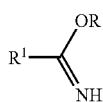

(4)

in which R is an alkyl group and $R^1$ has the aforementioned meaning, with an amine compound having the following formula (5):

$R^2NH_2$ (5)

in which $R^2$ has the aforementioned meaning, to give a reaction product, and a step of reacting the reaction product with at least one ketone compound having the following formula (3a) or (3b):

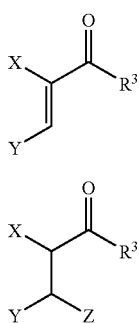

(3a)

(3b)

in which $R^3$ has the above-mentioned meaning, X is a leaving group, and each of Y and Z independently is a halogen atom, an alkoxy group, an aryloxy group, an alkylthio group, an arylthio group, a dialkylamino group or a diarylamino group, in the presence of a base.

In the processes for preparing the 1-substituted 5-acylimidazole compounds according to the invention, the particular embodiments are as follows:

(1) Each of $R^1$ and $R^3$ independently is an alkyl group having 1 to 6 carbon atoms which has no substituent group.

(2) $R^2$ is a secondary alkyl group having 3 to 6 carbon atoms which has no substituent group.

(3) $R^1$ is methyl.

(4) $R^2$ is isopropyl.

(5) $R^3$ is methyl.

(6) X is a halogen atom, such as bromine or iodine.

(7) The ketone compound has the formula (3a) in which Y is methoxy.

(8) The ketone compound has the formula (3a) in which Y is methoxy and X is bromine.

(9) Each of $R^1$ and $R^3$ is methyl, $R^2$ is isopropyl, and the ketone compound has the formula (3a) in which X is bromine and Y is methoxy.

(10) The ketone compound has the formula (3b) in which each of Y and Z is methoxy.

(11) The base is an organic amine compound such as a trialkylamine in which each alkyl independently has 1 to 6 carbon atoms.

(12) The N-substituted amidine compound reacts with the ketone compound in a polar solvent, such as an alkyl alcohol having 1 to 6 carbon atoms.

(13) The N-substituted amidine compound reacts with the ketone compound at a temperature in the range of 10 to 200° C.

EFFECTS OF THE INVENTION

The processes of the invention enable to prepare the 1-substituted 5-acylimidazole compounds in a high yield by simple procedures under mild conditions. Accordingly, the processes of the invention are favorably employable for preparing the 1-substituted 5-acylimidazole compounds in industry.

DETAILED DESCRIPTION OF THE INVENTION

The N-substituted amidine compound employed in the process of the invention has the aforementioned formula (2). In the formula (2), $R^1$ is a group not participating in the reaction between the N-substituted amidine compound of the formula (2) and the ketone compound of the formula (3a) or (3b) and typically is hydrogen or a hydrocarbyl (or hydrocarbon) group which has or does not have a substituent group. Examples of the hydrocarbyl groups include alkyl groups having 1 to 12 carbon atoms (e.g., methyl, ethyl, propyl, butyl, pentyl, hexyl, heptyl, octyl, nonyl and decyl), cycloalkyl groups having 3 to 8 carbon atoms (e.g., cyclopropyl, cyclobutyl, cyclopentyl, cyclohexyl, cycloheptyl, and cyclooctyl), aralkyl groups having $C_{1-3}$ alkyl moiety (e.g., phenethyl and phenylpropyl), monocyclic, dicyclic or tricyclic aryl groups having 6 to 14 carbon atoms (e.g., phenyl, p-tolyl, naphthyl, and anthryl), and monocyclic, dicyclic or tricyclic heterocyclic groups having 3 to 14 carbon atoms (e.g., pyridyl, pyridinyl, piperazinyl, pyrrolyl, imidazolyl, furyl, and thienyl). The hydrocarbyl groups can be in any isomer forms. $R^1$ particularly is an alkyl group and most particularly is methyl.

The hydrocarbyl groups may have one or more substituent groups. Examples of the substituent groups include a substituent group bonded via a carbon atom, a substituent group bonded via an oxygen atom, a substituent group bonded via a nitrogen atom, a substituent group bonded via a sulfur atom, and a halogen atom.

Examples of the substituent groups bonded via a carbon atom include alkyl groups having 1 to 12 carbon atoms such as methyl, ethyl, propyl, butyl, pentyl, and hexyl; cycloalkyl groups having 3 to 8 carbon atoms such as cyclopropyl, cyclobutyl, cyclopentyl, cyclohexyl, and cycloheptyl; alkenyl groups having 2 to 8 carbon atoms such as vinyl, allyl and propenyl; cycloalkenyl groups having 3 to 8 carbon atoms such as cyclopropenyl, cyclobutenyl and cyclopentenyl; heterocyclic groups such as quinolyl, pyridyl, pyrrolidinyl, pyrrolyl, furyl, and thienyl; aryl groups such as phenyl, tolyl, fluorophenyl, xylyl, biphenylyl, naphthyl, anthryl, and phenanthoryl; acyl groups such as $C_1$-$C_6$ alkanoyl groups, $C_1$-$C_6$ alkenoyl groups, $C_3$-$C_8$ cycloalkylcarbonyl and arylcarbonyl (e.g., acetyl, propionyl, acryloyl, pivaloyl, cyclohexylcarbonyl, benzoyl, naphthoyl, and toluoyl, which may be acetallized); carboxyl groups; $C_1$-$C_6$ alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups can be in the form of any isomers. These substituents can further have a substituent such as a $C_1$-$C_4$ alkyl group or a halogen atom.

Examples of the substituent groups bonded via an oxygen atom include hydroxyl; $C_1$-$C_6$ alkoxy groups such as methoxy, ethoxy, propoxy, butoxy, pentyloxy, hexyloxy, and heptyloxy; and aryloxy groups such as phenoxy, toluyloxy, and naphthyloxy. These groups can be in the form of any isomers. These substituents can further have a substituent such as a $C_1$-$C_4$ alkyl group or a halogen atom.

Examples of the substituent groups bonded via a nitrogen atom include primary amino groups such as N—($C_1$-$C_6$ alkyl) amino groups, $C_3$-$C_6$ cycloalkylamino groups and arylamino groups (e.g., methylamino, ethylamino, propylamino, butylamino, cyclohexylamino, phenylamino, and naphthylamino); secondary amino groups such as N,N—($C_1$-$C_6$ alkyl)amino groups and diarylamino groups (e.g., dimethylamino, diethylamino, dipropylamino, dibutylamino, methylethyl-amino, methylpropylamino, methylbutylamino, diphenyl-amino, and N-methyl-N-methanesulfonylamino); heterocyclic amino groups having a nitrogen atom as a ring-forming member, such as morpholino, piperidino, piperazinyl, pyrazolidinyl, pyrrolidino, and indolyl; and imino group. These groups can be in the form of any isomers. These substituents can further have a substituent such as a $C_1$-$C_4$ alkyl group or a halogen atom.

Examples of the substituent groups bonded via a sulfur atom include mercapto; thioalkoxy groups such as thiomethoxy, thioethoxy, and thiopropoxy; and thioaryloxy groups such as thiophenoxy, thiotoluoyloxy, and thionaphthyloxy. These groups can be in the form of any isomers. These substituents can further have a substituent such as a $C_1$-$C_4$ alkyl group or a halogen atom.

Accordingly, in one embodiment of the invention, $R^1$ is hydrogen, an alkyl group having 1 to 12 carbon atoms, a cycloalkyl group having 3 to 8 carbon atoms, an aralkyl group having a $C_1$-$C_3$ alkyl group, or a monocyclic, dicyclic or tricyclic aryl group having 6 to 14 carbon atoms. The alkyl groups, cycloalkyl groups, aralkyl groups and aryl groups can have one or more substituents (e.g., halogen atom, a $C_1$-$C_{12}$ alkyl group, a $C_3$-$C_8$ cyclo-alkyl group, a $C_2$-$C_8$ alkenyl group, a $C_3$-$C_8$ cycloalkenyl group, a heterocyclic group, an aryl group, a $C_1$-$C_6$ alkanoyl group, a $C_3$-$C_8$ cycloalkylcarbonyl group, an aryl-carbonyl group, a carboxyl group, a $C_1$-$C_6$ alkoxycarbonyl group, an aryloxycarbonyl group, trifluoromethyl, cyano, hydroxyl, a $C_1$-$C_6$ alkoxy group, an aryloxy group, an N—($C_1$-$C_6$ alkyl)amino group, a $C_3$-$C_8$ cycloalkylamino group, an arylamino group, an N,N-di($C_1$-$C_6$ alkyl)amino group, a diaryl amino group, N-methyl-N-methanesulfonylamino, imino, and mercapto). The aromatic ring of each of the aralkyl group and aryl group can further have a substituent such as a $C_1$-$C_4$ alkyl group or a halogen atom.

Examples of the halogen atoms include fluorine, chlorine, bromine, and iodine.

$R^2$ is a group selected from the group consisting of a secondary alkyl group, a tertiary alkyl group, and a cycloalkyl group. Examples of the secondary alkyl groups include secondary alkyl groups having 3 to 6 carbon atoms such as isopropyl, sec-butyl, 2-pentyl and 3-pentyl. Examples of the tertiary alkyl groups include tertiary alkyl groups having 4 to 7 carbon atoms such as t-butyl and 1,1-dimethylpropyl. Examples of the cycloalkyl groups include cycloalkyl groups having 3 to 8 carbon atoms such as cyclopropyl, cyclobutyl, cyclopentyl, cyclohexyl and cycloheptyl. These secondary or tertiary alkyl groups can further have substituents which are described for $R^1$. Particularly, secondary alkyl groups, (more particularly is isopropyl) can be mentioned.

Accordingly, in one embodiment of the invention, $R^2$ is a secondary alkyl group having 3 to 6 carbon atoms, a tertiary alkyl group having 4 to 7 carbon atoms, or a cycloalkyl group having 3 to 8 carbon atom, in which these groups can have one or more substituents (such as a halogen atom, an alkoxy group having 1 to 6 carbon atoms, or hydroxyl).

The N-substituted amidine compound can be in the form of a salt such as hydrochloride, hydrosulfide, sulfide or phosphate. Particularly, it is hydrochloride.

The N-substituted amidine compound of the formula (2) employed in the process of the invention can be prepared by reacting an imido-acid compound of the formula (4) and an amine compound of the formula (5). The reaction conditions are described in Bull. Soc. Chim. Fr II, 449 (1978). The reaction product (i.e., N-substituted amidine compound) produced in the above-mentioned reaction can be subjected to the reaction with the ketone compound without separating the reaction product from a reaction mixture.

The ketone compound employed in the process of the invention has the aforementioned formula (3a) or (3b). In the formulas (3a) and (3b), $R^3$ is a group not participating in the reaction between the N-substituted amidine compound of the formula (2) and the ketone compound and typically is a hydrocarbyl (or hydrocarbon) group which has or does not have a substituent group. Examples of the hydrocarbyl groups and substituents are the same as those described for $R^1$.

Accordingly, in one embodiment of the invention, $R^3$ is an alkyl group having 1 to 12 carbon atoms, a cycloalkyl group having 3 to 8 carbon atoms, an aralkyl group having a $C_1$-$C_3$ alkyl group, or a monocyclic, dicyclic or tricyclic aryl group having 6 to 14 carbon atoms. The alkyl groups, cycloalkyl groups, aralkyl groups and aryl groups can have one or more substituents (e.g., halogen atom, a $C_1$-$C_{12}$ alkyl group, a $C_3$-$C_8$ cycloalkyl group, a $C_2$-$C_8$ alkenyl group, a $C_3$-$C_8$ cycloalkenyl group, a heterocyclic group, an aryl group, a $C_1$-$C_6$ alkanoyl group, a $C_3$-$C_8$ cycloalkylcarbonyl group, an arylcarbonyl group, a carboxyl group, a $C_1$-$C_6$ alkoxycarbonyl group, an aryloxycarbonyl group, trifluoromethyl, cyano, hydroxyl, a $C_1$-$C_6$ alkoxy group, an aryloxy group, an N—($C_1$-$C_6$ alkyl)amino group, a $C_3$-$C_8$ cycloalkylamino group, an arylamino group, an N,N-di($C_1$-$C_6$ alkyl)amino group, a diaryl amino group, N-methyl-N-methanesulfonyl, imino, and mercapto). The aromatic ring of each of the aralkyl group and aryl group can further have a substituent such as a $C_1$-$C_4$ alkyl group or a halogen atom.

X is a leaving group such as a halogen atom (e.g., fluorine, chlorine, bromine, and iodine, particularly bromine and iodine).

Each of Y and Z can be independently a halogen atom (e.g., fluorine, chlorine, bromine, or iodine), an alkoxy group having 1 to 6 carbon atoms (e.g., methoxy and ethoxy), an aryloxy group (e.g., phenoxy), an alkylthio group having 1 to 6 carbon atoms (e.g., methylthio and ethylthio), an arylthio group (e.g., phenylthio), a dialkylamino group having 2 to 12 carbon atoms (e.g., dimethylamino and diethylamino), and a diarylamino group (e.g., diphenylamino). Particularly, it is an alkoxy group, and more particularly it is methoxy.

Accordingly, in one embodiment of the invention, each of Y and Z independently is a halogen atom, an alkoxy group having 1 to 6 carbon atoms, an aryloxy group, an alkylthio group having 1 to 6 carbon atoms, an arylthio group, a dialkylamino group having 2 to 12 carbon atoms (that is, N,N—($C_1$-$C_6$ alkyl)$_2$ amino group), or a diarylamino group.

Accordingly, in one aspect, the present invention provides a process for preparing a 1-substituted 5-acyl-imidazole compound of the following formula (1):

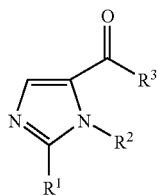

(1)

which comprises reacting an N-substituted amidine compound having the following formula (2) or a salt thereof:

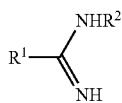

(2)

with at least one ketone compound having the following formula (3a) or (3b):

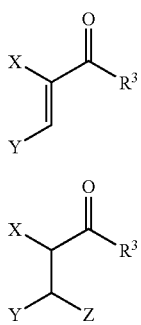

(3a)

(3b)

in the presence of a base.

In the above-mentioned formulas, each of $R^1$, $R^2$, $R^3$, X and Y has the following meaning:

$R^1$ is hydrogen, an alkyl group having 1 to 12 carbon atoms, a cycloalkyl group having 3 to 8 carbon atoms, an aralkyl group having a $C_1$-$C_3$ alkyl group, or a monocyclic, dicyclic or tricyclic aryl group having 6 to 14 carbon atoms. The alkyl groups, cycloalkyl groups, aralkyl groups and aryl groups can have one or more substituents (e.g., halogen atom, a $C_1$-$C_{12}$ alkyl group, a $C_3$-$C_8$ cycloalkyl group, a $C_2$-$C_8$ alkenyl group, a $C_3$-$C_8$ cycloalkenyl group, a heterocyclic group, an aryl group, a $C_1$-$C_6$ alkanoyl group, a $C_3$-$C_8$ cycloalkylcarbonyl group, an aryl-carbonyl group, a carboxyl group, a $C_1$-$C_6$ alkoxycarbonyl group, an aryloxycarbonyl group, trifluoromethyl, cyano, hydroxyl, a $C_1$-$C_6$ alkoxy group, an aryloxy group, an N—($C_1$-$C_6$ alkyl)amino group, a $C_3$-$C_8$ cycloalkylamino group, an arylamino group, an N,N-di($C_1$-$C_6$ alkyl) amino group, a di-aryl amino group, N-methyl-N-methanesulfonyl, imino, and mercapto), and the aromatic ring of each of the aralkyl group and aryl group can further have a substituent such as a $C_1$-$C_4$ alkyl group or a halogen atom;

$R^2$ is a secondary alkyl group having 3 to 6 carbon atoms, a tertiary alkyl group having 4 to 7 carbon atoms, or a cycloalkyl group having 3 to 8 carbon atom, in which these groups can have one or more substituents (such as a halogen atom, an alkoxy group having 1 to 6 carbon atoms, or hydroxyl);

$R^3$ is an alkyl group having 1 to 12 carbon atoms, a cycloalkyl group having 3 to 8 carbon atoms, an aralkyl group having a $C_1$-$C_3$ alkyl group, or a monocyclic, di-cyclic or tricyclic aryl group having 6 to 14 carbon atoms. The alkyl groups, cycloalkyl groups, aralkyl groups and aryl groups can have one or more substituents (e.g., halogen atom, a $C_1$-$C_{12}$ alkyl group, a $C_3$-$C_8$ cyclo-alkyl group, a $C_2$-$C_8$ alkenyl group, a $C_3$-$C_8$ cycloalkenyl group, a heterocyclic group, an aryl group, a $C_1$-$C_6$ alkanoyl group, a $C_3$-$C_8$ cycloalkylcarbonyl group, an aryl-carbonyl group, a carboxyl group, a $C_1$-$C_6$ alkoxycarbonyl group, an aryloxycarbonyl group, trifluoromethyl, cyano, hydroxyl, a $C_1$-$C_6$ alkoxy group, an aryloxy group, an N—($C_1$-$C_6$ alkyl)amino group, a $C_3$-$C_8$ cycloalkylamino group, an arylamino group, an N,N-di($C_1$-$C_6$ alkyl)amino group, a diaryl amino group, N-methyl-N-methanesulfonylamino, imino, and mercapto), and the aromatic ring of each of the aralkyl group and aryl group can further have a substituent such as a $C_1$-$C_4$ alkyl group or a halogen atom;

X is a halogen atom; and each of Y and Z independently is a halogen atom, an alkoxy group having 1 to 6 carbon atoms, an aryloxy group, an alkylthio group having 1 to 6 carbon atoms, an arylthio group, a dialkylamino group having 2 to 12 carbon atoms, or a diarylamino group.

In another aspect, the invention provides a process for preparing for preparing a 1-substituted 5-acyl-imidazole compound of the following formula (1):

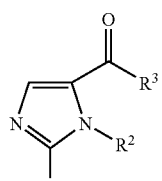

(1)

[in which $R^1$ is methyl, $R^2$ is isopropyl, and $R^3$ is methyl] which comprises reacting an N-substituted amidine compound having the following formula (2) or a salt thereof:

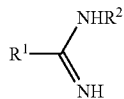

(2)

[in which each of R¹ and R² is the same as above] with at least one ketone compound having the following formula (3a) or (3b):

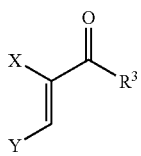

(3a)

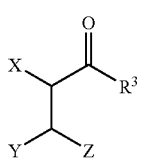

(3b)

[in which R³ is the same as above, X is a halogen atom, and each of Y and Z is methoxy], in the presence of a base.

Examples of the bases employed in the reaction include an organic amine compound such as trialkylamine compounds which have an alkyl group each containing 1 to 6 carbon atoms, such as triethylamine, tripropylamine and tributylamine, and heterocyclic compounds such as pyridine and picoline, and an inorganic base compounds such as an alkali metal hydroxide (e.g., sodium hydroxide and potassium hydroxide), an alkali metal carbonate (e.g., sodium carbonate and potassium carbonate), an alkali metal hydrogen carbonate (e.g., sodium hydrogen carbonate and potassium hydrogen carbonate), and an alkali metal alkoxide (e.g., sodium methoxide, potassium methoxide, sodium ethoxide, potassium ethoxide, sodium t-butoxide, and potassium t-butoxide). Particularly, it is an organic amine compound, and specifically a trialkylamine compound. More particularly, it is a triethylamine. The bases can be employed singly or in combination.

The base can be employed in the reaction in an amount of 0.1 to 20 moles, particularly 0.5 to 10 moles, per one mole of the N-substituted amidine compound or its salt.

The reaction can be performed in a solvent (particularly a polar solvent). Examples of the polar solvents include water, a lower alkyl alcohol having 1 to 6 carbon atoms (e.g., methanol, ethanol, isopropyl alcohol and t-butyl alcohol), a ketone compound (e.g., acetone, methyl ethyl ketone, and methyl isobutyl ketone), an amide compound (e.g., N,N-dimethylformamide, N,N-dimethylacet-amide, N-methylpyrrolidone), a urea (e.g., N,N'-dimethylimidazolidinone), a sulfoxide (e.g., dimethylsulfoxide), a sulfone (e.g., sulforane), a nitrile (e.g., acetoni-trile and propionitrile), and an ether (e.g., diethyl ether, diisopropyl ether, dimethoxyethane, tetrahydrofuran, 2-methyltetrahydrofuran, and dioxane). The solvent can be employed singly or in combination.

The solvent can be employed in an amount of 0.5 to 100 mL, particularly 1 to 50 mL, per one gram of the N-substituted amidine compound or its salt.

The invention can be carried out, for instance, by mixing the N-substituted amidine compound or its salt, the ketone compound, a base, and a solvent and stirring the mixture at 10 to 200° C., preferably 20 to 120° C. There is no specific limitation with respect to the reaction pressure.

The 1-substituted 5-acylimidazole compound prepared by the reaction can be isolated and purified by conventional methods such as neutralization, extraction, filtration, concentration, distillation, recrystallization, crystallization, and column chromatography.

The present invention is further described by the following non-limiting examples.

REFERENCE EXAMPLE 1

Preparation of an Isopropyl Alcohol Solution of N-isopropylacetamidine

In a 300 mL-volume glass vessel equipped with a stirrer, a thermometer and a dropping funnel, 20.0 g (0.162 mol) of ethyl acetimidate and 80 mL of isopropyl alcohol were placed. To the mixture in the vessel, 16.4 g (0.162 mol) of triethylamine was dropwise added, while the mixture was kept at a temperature of not higher than 30° C. The mixture was stirred for 10 minutes at room temperature and then cooled to 10° C. To the cooled mixture was dropwise added 9.56 g (0.162 mol) of isopropylamine, while the mixture was kept at a temperature of not higher than 30° C. The mixture was then stirred for one hour at room temperature for carrying out reaction. After the reaction was complete, the reaction mixture was concentrated to give an isopropyl alcohol solution containing 16.2 g (0.162 mol) of N-isopropylacetamidine.

EXAMPLE 1

Preparation of 5-acetyl-1-isopropyl-2-methylimidazole

In a 300 mL-volume glass vessel equipped with a stirrer, a thermometer and a dropping funnel, the isopropyl alcohol solution containing 16.2 g (0.162 mol) of N-isopropylacetamidine (which was prepared in the above-mentioned Reference Example 1), 19.3 g (0.108 mol) of 3-bromo-4-methoxy-3-buten-2-one and 16.4 g (0.162 mol) of triethylamine were placed. The mixture was heated to 80° C. under stirring for 8 hours, for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was distilled under reduced pressure (0.4 kPa, 85° C.) to give 10.9 g (yield: 61%) of 5-acetyl-1-isopropyl-2-methylimidazole as pale yellow liquid.

The produced 5-acetyl-1-isopropyl-2-methylimidazol had the following physical properties:

$^1$H-NMR (CDCl$_3$, δ (ppm)): 1.50 (6H, d), 2.45 (3H, s), 2.52 (3H, s), 5.30 (1H, m), 7.71 (1H, s);

CI-MS (m/e): 167 (MH), 151 (M-Me), 109 (M-NiPr).

EXAMPLE 2

Preparation of 5-acetyl-1-isopropyl-2-methylimidazole

In a 300 mL-volume glass vessel equipped with a stirrer, a thermometer and a dropping funnel, the isopropyl alcohol solution containing 16.2 g (0.162 mol) of N-isopropylacetamidine (which was prepared in the above-mentioned Reference Example 1), 22.8 g (0.108 mol) of 3-bromo-4,4-dimethoxy-2-butanone and 16.4 g (0.162 mol) of triethylamine were placed. The mixture was heated to 80° C. under stirring for 20 hours, for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was distilled under reduced pressure (0.4 kPa, 85° C.) to give 9.63 g (yield: 54%) of 5-acetyl-1-isopropyl-2-methylimidazol as pale yellow liquid.

REFERENCE EXAMPLE 2

Preparation of an Isopropyl Alcohol Solution of N—((R)-1-phenylethyl)acetamidine The procedures of Reference Example 1 were repeated except that isopropylamine was replaced with 19.6 g (0.162 mol) of (R)-1-phenylethylamine. There was obtained an isopropyl alcohol solution containing 26.2 g (0.162 mol) of N—((R)-1-phenylethyl)acetamidine.

EXAMPLE 3

Preparation of 5-acetyl-2-methyl-1-((R)-1-phenyl-ethyl)imidazole

In a 300 mL-volume glass vessel equipped with a stirrer, a thermometer and a dropping funnel, the isopropyl alcohol solution containing 26.2 g (0.162 mol) of N—((R)-1-phenylethyl)acetamidine (which was prepared in the above-mentioned Reference Example 2), 19.3 g (0.108 mol) of 3-bromo-4-methoxy-3-buten-2-one and 16.4 g (0.162 mol) of triethylamine were placed. The mixture was heated to 80° C. under stirring for 8 hours for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was purified by silica gel column chromatography (eluant: ethyl acetate) to give 18.7 g (yield: 76%) of 5-acetyl-2-methyl-1-((R)-1-phenylethyl)imidazole.

The produced 5-acetyl-2-methyl-1-((R)-1-phenyl-ethyl)imidazole had the following physical properties:
$^1$H-NMR (CDCl$_3$, δ (ppm)): 1.85 (3H, d), 2.06 (3H, s), 2.49 (3H, s), 6.93 (1H, m), 7.13 (2H, m), 7.32 (3H, m), 7.78 (1H, s);
CI-MS (m/e): 229 (MH).

REFERENCE EXAMPLE 3

Preparation of an N-tert-butyl-acetamidine

In a 300 mL-volume glass vessel equipped with a stirrer, a thermometer and a dropping funnel, 20.0 g (0.162 mol) of ethyl acetimidate and 80 mL of isopropyl alcohol were placed. To the mixture in the vessel, 16.4 g (0.162 mol) of triethylamine was dropwise added, while the mixture was kept at a temperature of not higher than 30° C. The mixture was then stirred for 10 minutes at room temperature. The mixture was then cooled to 10° C. To the cooled mixture was dropwise added 11.8 g (0.162 mol) of tert-butylamine, while the mixture was kept at a temperature of not higher than 30° C. The mixture was then stirred for one hour at room temperature for carrying out reaction. After the reaction was complete, the reaction mixture was purified by silica gel column chromatography (eluant: ethyl acetate/methanol=20/1) to give 15.9 g (yield: 86%) of N-tert-butylacetamidine.

The produced N-tert-butylacetamidine had the following physical properties:
$^1$H-NMR (CD$_3$OD, δ (ppm)): 1.43 (9H, s), 2.21 (3H, s), 3.35 (2H, s);
CI-MS (m/e): 115 (MH).

EXAMPLE 4

Preparation of 5-acetyl-1-tert-butyl-2-methylimidazole

In a 300 mL-volume glass vessel equipped with a stirrer, a thermometer and a dropping funnel, 18.5 g (0.162 mol) of N-tert-butylacetamidine (which was prepared in the above-mentioned Reference Example 3), 19.3 g (0.108 mol) of 3-bromo-4-methoxy-3-buten-2-one and 16.4 g (0.162 mol) of triethylamine were placed. The mixture was heated to 120° C. under stirring for 8 hours for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was purified by silica gel column chromatography (eluant: ethyl acetate) to give 4.86 g (yield: 25%) of 5-acetyl-1-tert-butyl-2-methyl-imidazole.

The produced 5-acetyl-1-tert-butyl-2-methylimidazole had the following physical properties:
$^1$H-NMR (CDCl$_3$, δ (ppm)): 1.72 (9H, s), 2.49 (3H, s), 2.65 (3H, s), 7.70 (1H, s)
CI-MS (m/e): 181 (MH)

REFERENCE EXAMPLE 4

Preparation of an Isopropyl Alcohol Solution of N-cyclopropylacetamidine

The procedures of Reference Example 1 were repeated except that isopropylamine was replaced with 9.23 g (0.162 mol) of cyclopropylamine. There was obtained an isopropyl alcohol solution containing 15.9 g (0.162 mol) of N-cyclopropylacetamidine.

EXAMPLE 5

Preparation of 5-acetyl-1-cyclopropyl-2-methylimidazole

In a 300 mL-volume glass vessel equipped with a stirrer, a thermometer and a dropping funnel, the isopropyl alcohol solution containing 15.9 g (0.162 mol) of N-cyclopropylacetamidine (which was prepared in the above-mentioned Reference Example 4), 19.3 g (0.108 mol) of 3-bromo-4-methoxy-3-buten-2-one and 16.4 g (0.162 mol) of triethylamine were placed. The mixture was heated to 80° C. under stirring for 8 hours for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was purified by silica gel column chromatography (eluant: hexane/ethyl acetate=2/1) to give 11.8 g (yield: 67%) of 5-acetyl-1-cyclopropyl-2-methylimidazole as pale yellow liquid.

The produced 5-acetyl-1-cyclopropyl-2-methylimidazole had the following physical properties:

$^1$H-NMR (CDCl$_3$, δ (ppm)): 0.69 (2H, m), 0.78 (2H, m), 2.28 (3H, s), 2.33 (3H, s), 2.81 (1H, m), 5.41 (1H, m), 7.66 (1H, s);

CI-MS (m/e): 165 (MH).

REFERENCE EXAMPLE 5

Preparation of an Isopropyl Alcohol Solution of N-isopropylformamidine

The procedures of Reference Example 1 were repeated except that ethyl acetimidate was replaced with 7.29 g (0.162 mol) of formamide and that the reaction temperature was 50° C. There was obtained an isopropyl alcohol solution containing 13.9 g (0.162 mol) of N-isopropyl-formamidine.

EXAMPLE 6

Preparation of 5-acetyl-1-isopropylimidazole

In a 300 mL-volume glass vessel equipped with a stirrer, a thermometer and a dropping funnel, the isopropyl alcohol solution containing 13.9 g (0.162 mol) of N-isopropylformamidine (which was prepared in Reference Example 4), 19.3 g (0.108 mol) of 3-bromo-4-methoxy-3-buten-2-one and 16.4 g (0.162 mol) of triethylamine were placed. The mixture was heated to 8° C. under stirring for 8 hours for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was purified by silica gel column chromatography (eluant: ethyl acetate) to give 3.28 g (yield: 20%) of 5-acetyl-1-isopropylimidazole as pale yellow liquid.

The produced 5-acetyl-1-isopropylimidazole had the following physical properties:

$^1$H-NMR (DMSO-d$_6$, δ (ppm)): 1.40 (6H, d, J=6.59 Hz), 2.43 (3H, s), 5.16 (1H, sep, J=6.59 Hz), 7.93 (1H, d), 8.15 (1H, brs);

CI-MS (m/e): 153 (MH).

EXAMPLE 7

Preparation of 5-benzoyl-1-isopropyl-2-methylimidazole

In a 300 mL-volume glass vessel equipped with a stirrer, a thermometer and a dropping funnel, the isopropyl alcohol solution containing 16.2 g (0.162 mol) of N-isopropylacetamidine (which was prepared in the same manner as in Reference Example 1), 26.0 g (0.108 mol) of 2-bromo-3-methoxy-1-phenyl-2-propen-1-one and 16.4 g (0.162 mol) of triethylamine were placed. The mixture was heated to 80° C. under stirring for 8 hours for carrying out reaction. After the reaction was complete, 80 mL of sulfuric acid (2 mol/L) was added to the reaction mixture, and the mixture was concentrated under reduced pressure. The concentrate was washed with methyl isobutyl ketone, and the aqueous portion was taken out. The aqueous portion was made basic by adding an aqueous 48% sodium hydroxide, while the mixture was kept at a temperature of not higher than 40° C. The aqueous basic portion was subjected to extraction with methyl isobutyl ketone, and the extracted portion was concentrated under reduced pressure. The concentrate was purified by silica gel column chromatography (eluant: hexane/ethyl acetate=2/1) to give 2.47 g (yield: 10%) of 5-benzoyl-1-isopropyl-2-methylimidazole as pale yellow liquid.

The produced 5-benzoyl-1-isopropyl-2-methylimidazole had the following physical properties:

$^1$H-NMR (CDCl$_3$, δ (ppm)): 1.60 (6H, d), 2.60 (3H, s), 5.20 (1H, m), 7.48 (2H, m), 7.59 (2H, m), 7.81 (1H, s), 7.83 (1H, m);

CI-MS (m/e): 229 (MH).

What is claimed is:

1. A process for preparing a 1-substituted 5-acyl-imidazole compound having the following formula (1):

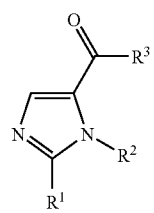

(1)

in which

R$^1$ is a hydrogen atom or an optionally substituted hydrocarbyl group;

R$^2$ is a secondary alkyl group, a tertiary alkyl group or a cycloalkyl group, wherein each group is optionally substituted; and R$^3$ is an optionally substituted hydrocarbyl group, which comprises reacting an N-substituted amidine compound having the following formula (2):

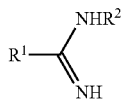

(2)

in which each of $R^1$ and $R^2$ is as defined above, or a salt thereof, with at least one ketone compound having the following formula (3a) or (3b):

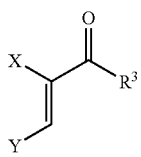

(3a)

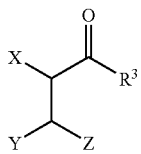

(3b)

in which $R^3$ is as defined above,

X is a leaving group, and each of Y and Z is independently a halogen atom, an alkoxy group, an aryloxy group, an alkylthio group, an arylthio group, a dialkylamino group or a diarylamino group, in the presence of a base.

2. The process according to claim 1, which each of $R^1$ and $R^3$ is independently an unsubstituted alkyl group having 1 to 6 carbon atoms.

3. The process according to claim 1, in which $R^2$ is a secondary unsubstituted alkyl group having 3 to 6 carbon atoms.

4. The process according to claim 1, in which $R^1$ is methyl.

5. The process according to claim 1, in which $R^2$ is isopropyl.

6. The process according to claim 1, in which $R^3$ is methyl.

7. The process according to claim 1, in which X is a halogen atom.

8. The process according to claim 1, in which X is a bromine atom or an iodine atom.

9. The process according to claim 1, in which the ketone compound has the formula (3a) in which Y is methoxy.

10. The process according to claim 1, in which the ketone compound has the formula (3b) in which each of Y and Z is methoxy.

11. The process according to claim 1 wherein an N-substituted amidine compound having the following formula (2):

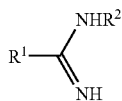

(2)

in which $R^1$ is methyl and $R^2$ is isopropyl, or a salt thereof, is reacted with at least one ketone compound having the following formula (3a) or (3b):

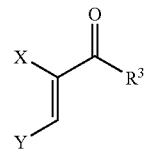

(3a)

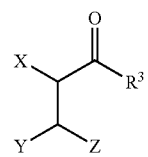

(3b)

in which $R^3$ is methyl, X is a halogen atom, and each of Y and Z is methoxy, in the presence of a base.

12. The process according to claim 1, in which the base is an organic amine compound.

13. The process according to claim 1, in which the base is a trialkylamine in which each alkyl independently has 1 to 6 carbon atoms.

14. The process according to claim 1, in which the N-substituted amidine compound reacts with the ketone compound in a polar solvent.

15. The process according to claim 1, in which the N-substituted amidine compound reacts with the ketone compound in a polar solvent wherein the polar solvent is an alkyl alcohol having 1 to 6 carbon atoms.

16. The process according to claim 1, in which the N-substituted amidine compound reacts with the ketone compound at a temperature in the range of 10 to 200° C.

17. A process for preparing a 1-substituted 5-acylimidazole compound having the following formula (1):

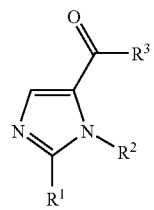

(1)

in which $R^1$ is a hydrogen atom or an optionally substituted hydrocarbyl group;

$R^2$ is a secondary alkyl group, a tertiary alkyl group or a cycloalkyl group, wherein each group is optionally substituted; and $R^3$ is an optionally substituted hydrocarbyl group, which comprises reacting an imido-acid compound having the following formula (4):

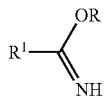

in which R is an alkyl group and $R^1$ is as defined above, with an amine compound having the following formula (5):

in which $R^2$ is as defined above,
to give a reaction product, and
reacting the reaction product with at least one ketone compound having the following formula (3a) or (3b):

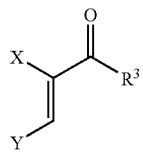

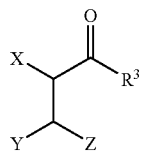

in which $R^3$ is as defined above, X is a leaving group, and each of Y and Z is independently a halogen atom, an alkoxy group, an aryloxy group, an alklthio group, an arylthio group, a dialkylamino group or a diarylamino group, in the presence of a base.

18. The process according to claim 17, in which each of $R^1$ and $R^3$ is methyl, and $R^2$ is isopropyl.

19. The process according to claim 17, in which the base is an organic amine compound.

20. The process according to claim 17, in which the base is a trialkylamine in which each alkyl independently has 1 to 6 carbons.

21. The process according to claim 17, in which the reaction product of the imino-acid compound of formula (4) with the amine compound of formula (5) reacts with the ketone compound in a polar solvent.

22. The process according to claim 17, in which the reaction product of the imino-acid compound of formula (4) with the amine compound of formula (5) reacts with the ketone compound in a polar solvent wherein the polar solvent is an alkyl alcohol having 1 to 6 carbon atoms.

23. The process according to claim 17, in which the reaction product of the imino-acid compound of formula (4) with the amine compound of formula (5) reacts with the ketone compound at a temperature in the range of 10 to 200° C.

\* \* \* \* \*